United States Patent [19]

Kawamura et al.

[11] Patent Number: 5,227,473

[45] Date of Patent: Jul. 13, 1993

[54] QUINONE DIAZIDE COMPOUND AND LIGHT-SENSITIVE COMPOSITION CONTAINING SAME

[75] Inventors: Kouichi Kawamura; Satoshi Takita, both of Shizuoka, Japan

[73] Assignee: Fuji Photo Film Co., Ltd., Minami-ashigara, Japan

[21] Appl. No.: 698,108

[22] Filed: May 10, 1991

[30] Foreign Application Priority Data

May 18, 1990 [JP] Japan ................................ 2-128378

[51] Int. Cl.$^5$ ...................... C09B 23/01; C09B 15/00; C09B 57/02; G03C 1/72
[52] U.S. Cl. ................................... 534/557; 534/556; 430/189; 430/190; 430/192; 430/193
[58] Field of Search ................ 534/556, 557; 430/192, 430/193

[56] References Cited

U.S. PATENT DOCUMENTS

| | | | |
|---|---|---|---|
| 3,046,115 | 7/1962 | Schmidt et al. | 534/557 X |
| 3,046,121 | 7/1962 | Schmidt et al. | 534/557 X |
| 3,102,809 | 9/1963 | Endermann et al. | 534/557 X |
| 3,674,495 | 7/1972 | Esaka | 534/557 X |
| 4,758,497 | 7/1988 | Shah et al. | 534/557 X |
| 4,818,658 | 4/1989 | Martin et al. | 534/557 X |

FOREIGN PATENT DOCUMENTS 62-36663  2/1987  Japan ................................ 534/557
63-261258 10/1988 Japan ................................ 430/193

Primary Examiner—Mary C. Lee
Assistant Examiner—Fiona T. Powers
Attorney, Agent, or Firm—Burns, Doane, Swecker & Mathis

[57] ABSTRACT

A quinone diazide of formula (I) or formula (II):

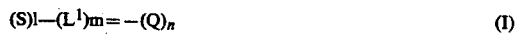

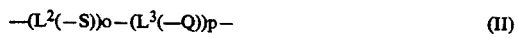

wherein S is a light absorbing portion having an absorption coefficient of greater than 1000 in wavelengths longer than 360 nm; Q is a quinone diazide residue; $L^1$, $L^2$ and $L^3$ are connecting groups connecting S and Q, provided, however, that $L^1$, $L^2$ and $L^3$ do not conjugate S and Q; l, m, n, o and p are integers; and wherein the emission intensity of the compound of formulas (I) and (II) is smaller than the emission intensity of the chromophoric group alone. Also disclosed is a light sensitive composition comprising an alkali soluble resin and the above quinone diazide compound. The quinone diazide compound of the present invention have spectral sensitization with respect to visible light and are useful in visible light projection plates and as visible laser sensing materials.

11 Claims, No Drawings

QUINONE DIAZIDE COMPOUND AND LIGHT-SENSITIVE COMPOSITION CONTAINING SAME

BACKGROUND OF THE INVENTION

The present invention relates to a novel quinone diazide compound spectrally sensitized in the visible region and a light-sensitive composition containing the novel compound The present invention also relates to a light-sensitive composition comprising the novel compound, and a photo-sensitive lithographic printing plate comprising the novel compound as a constituent of the light-sensitive layer.

It is a commonly-known fact that quinone diazide compounds have come to be widely used, in combination with alkali-soluble resins, in the field of photosensitive plates and resists. For example, reference is made to J. Kosar, *Light Sensitive Systems* (John Wiley & Sons 1965), and A. Reiser, *Photoreactive Polymers* (John Wiley & Sons 1989).

In recent years, image formation methods have been studied which utilize light sources other than state of the art ultraviolet light, such as visible light or near-infra red lasers. Presently, in the making of printing plates, the UV projector light beam method, directly laser-made plates, laser facsimile, holography, etc., have all already reached the practical stage. High sensitivity photosensitive materials which react with these light sources are just being developed. In developing light-sensitive materials for the above-used light sources, the existence of chemical compounds that react with high efficiency to light from the near ultraviolet to the visible and further to the near infra-red region is essential.

The light sensitization in the visible region of various, copolymer-utilizing light-sensitive compositions has been studied. A few of these high-sensitivity light-sensitive compositions are approaching the practical stage as visible light projection plates or visible light laser sensitive materials.

Nevertheless, in spite of the fact that light-sensitive compositions using quinone diazide compounds have been long studied, until now, reports of quinone diazides having spectral sensitization in the visible region are extremely rare, and no spectrally sensitized compounds have yet been proposed which have a degree of sensitivity so that they could be practically used.

SUMMARY OF THE INVENTION

The number one object of the present invention is therefore to offer a quinone diazide compound having high spectral sensitization with respect to visible light.

The number two object of the present invention is to offer a light-sensitive composition including the above quinone diazide compound.

The number three object of the present invention is to offer a light-sensitive composition including the above quinone diazide compound and an alkali soluble resin.

In accordance with the above objects, the present invention provides a compound having at least one quinone diazide portion Q and, included on the same molecule, at least one light absorbing group S which is a chromophoric group unconjugated with the quinone diazide portion and has a light absorption coefficient on the long wavelength side of 360 nm of greater than 1000, the emission intensity of the compound being smaller than that of a light absorbing compound SH having the same chromophoric group as the light absorbing portion S. "Emission intensity" as used here means the magnitude of fluorescence or phosphorescence.

According to the preferred embodiment of the present invention, there is provided a quinone diazide of formula (I) or formula (II):

In the above formulas, S is a light absorbing portion having an absorption coefficient of greater than 1000 in wavelengths longer than 360 nm; Q is a quinone diazide residue. The variables $L^1$, $L^2$ and $L^3$ are connecting groups connecting S and Q, provided, however, that $L^1$, $L^2$ and $L^3$ do not conjugate S and Q. The variables l, m, n, o and p are integers. According to the invention, the emission intensity of the compound of formulas (I) and (II) is smaller than the emission intensity of the chromophoric group alone, or a compound SH comprising substantially only the chromophoric group.

According to a preferred embodiment of the present invention, l is 1-5, m is 1-5, n is 1-15, o is 3-200, and p is 3-500. In another preferred embodiment, l is 1-3, m is 1-2, n is 1-8, o is 5-50, and p is 10-200. S is preferably selected from the group of merocyanine dyes, cyanine dyes, acridine dyes, xanthene dyes, and coumarine dyes. S may also be an arylidene dye of the formula (III):

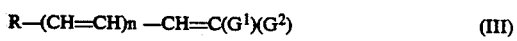

In formula (III), R is a substituted or unsubstituted aromatic ring having from 6 to 20 carbon atoms, or an hetero aromatic ring. $G^1$ and $G^2$ are the same or different and each represent a hydrogen atom, a cyano group, an alkoxycarbonyl group, a substituted alkoxy carbonyl group, an aryloxy carbonyl group, a substituted aryloxy carbonyl group, an acyl group, a substituted acyl group, an aryl carbonyl group, a substituted aryl carbonyl group, an aryl thio group, an alkyl sulfonyl group, an allyl sulfonyl group, or a fluoro alkyl sulfonyl group, provided, however, that $G^1$ and $G^2$ can not both be simultaneously hydrogen. $G^1$ and $G^2$ may combine with the carbon atom to which they are bonded to form a ring of non-metallic atoms. The variable n is 0 or 1.

Q is preferably selected from p-quinone diazide compounds and ortho quinone diazide compounds.

According to yet another embodiment of the present invention, there is provided a light sensitive composition comprising an alkali soluble resin and a quinone diazide compound of the above formula (I) or (II).

A still further embodiment of the present invention provides a photo-sensitive lithographic printing plate comprising a support and a light sensitive layer deposited thereon. The light sensitive layer comprises an alkali soluble resin and the quinone diazide compound of formula (I) or (II)

Further objects, features and advantages of the present invention will become apparent in view of the detailed description of preferred embodiments which follows when considered together with the accompanying working examples and comparative examples.

DETAILED DESCRIPTION OF THE PREFERRED EMBODIMENTS

Quinone diazide compounds do not absorb in the visible region, particularly not above 450 nm. Therefore, in order to make them sensitive to visible light, it is necessary to sensitize them by using visible-light-absorbing compounds (dyes). In other words, it is necessary to make the quinone azide decompose by causing the dye to absorb light and transmitting the energy from the excited dye to the quinone, through either of the processes of energy transfer or electron transfer. In order for the sensitization to be efficient, it is necessary that the energy transmission from the excited dye to the quinone diazide proceed efficiently. Whether the energy transmission method is by the energy transfer mechanism, or by the electron transfer mechanism, in order for the transmission to proceed efficiently, it is necessary that at least the following three conditions be present.

1. That the excitation lifetime of the dye be long.
2. That there be an appropriate relationship between the energy levels or oxidation potentials of the dye and the quinone diazide.
3. That the separation between the dye and quinone diazide molecules be small.

In photo-reactions in solvents, the third point is not a problem to the extent that collisions take place because of diffusion movement, but becomes an important factor in the films in which the light-sensitive composition is actually used because diffusion movement is very limited. In other words, it is important that the dye and the quinone diazide reside at very close separation.

These matters are described in N. J. Turro, *Modern Molecular Photochemistry*, Volume 9 (Benjamin/Cummings Publishing Co. 1978), and N. J. Turro, *Chemical Review*, Volume 86, pp. 401–449. They are also described in M. A. Fox, M. Chanon, eds., Photoinduced Electron Transfer: Part A, the essay starting at page 161.

The present inventors, in order to make the spectral sensitization of quinone diazides more efficient, and as a result of zealous research continuing to take into account the above three conditions, have come to the discovery that certain specific quinone diazide compounds decompose efficiently even in visible light.

The present invention provides a compound having at least one quinone diazide portion Q and, included on the same molecule, at least one light absorbing group S which is a chromophoric group unconjugated with the quinone diazide portion and has a light absorption coefficient on the long wavelength side of 360 nm of greater than 1000, the emission intensity of the compound being smaller than that of a light absorbing compound SH having the same chromophoric group as the light absorbing portion S.

Specifically, the present invention relates to the chain type compound of dye and quinone diazide expressed by general formula (I), or the high molecular compound including dye and quinone diazide as structural components expressed by general formula (II).

(S)l—(L¹)m—(Q) .  (I)

—(L²(—S)). —(L³(—Q))p —  (II)

In the formulas, S is a light absorbing portion having an absorption coefficient of greater than 1000 in wavelengths longer than 360 nm; Q is a quinone diazide residue; L¹, L² and L³ are connecting groups connecting S and Q; l, m, n, o and p are integers, l is 1–5, preferably 1–3, m is 1–5, preferably 1–2, n is 1–15, preferably 1–8, o is 3–200, preferably 5–50, p is 3–500, preferably 10–200. The emission intensity of the compounds expressed by general formulas (I) and (II) has the characteristic that it is smaller than the emission intensity of a light absorbing compound SH having the same chromophoric group as the light absorbing grgup S. The compound SH, which includes the light absorbing portion S having an absorption coefficient of greater than 1000 in wavelengths greater than 360 nm, may be a dye used in the art as a sensitizing dye such as a trichloromethyl-s-triazine type photopolymerization initiator, or an azinium salt type photopolymerization initiator. Concrete examples are merocyanine dyes described in U.S. Pat. Nos. 4,481,276, 4,399,211, and 4,810,618; cyanine dyes described in DE-A 3541534 and Japanese Unexamined Patent Publication (hereinafter Kokai) No. Sho 58-29803; acridine dyes such as acridine orange described in U.S. Pat. No. 4,845,011; thiapyrylium dyes such as 4(4-methoxy phenyl)-2,6-diphenyl thiapyrylium salt described in Japanese Kokai No. Sho 58-40302; arylidene dyes described in Japanese Kokai No. Sho 47-13103; cyanine dyes having oxocarbon-bridged nuclei such as squalilium; multi-nuclei aromatic compounds such as 9,10-diethyl anthracene, and pyrene; xanthene type dyes such as eosin, erythrosine, and fluorescein. All of the above concrete examples are described together with cyanine, merocyanine, and acridine type dyes in U.S. Pat. Nos. 4,743,529, 4,743,530, 4,743,531. The coumarin compounds described in U.S. Pat. No. 4,743,531 and Research Disclosure, volume 200, December 1980, item 20036 can also be used. In addition, one can use hetero aromatic compounds such as acridone and thioxanthone; amino aromatic compounds such as amino-substituted chalcone; porphyrin dyes; and phthalocyanine dyes. Particularly preferred among these dyes are dyes having an absorption coefficient greater than 1000 on the long wavelength side of 400 nm. Specifically, there are merocyanine dyes, cyanine dyes, acridine type dyes, multinuclear aromatic compounds, xanthene type dyes, coumarine type dyes, hetero aromatic compounds, and the arylidene dyes of the below general formula (III).

R—(CH=CH)n—CH=C(G¹)(G²)  (III)

In the formula, R represents a substituted or unsubstituted aromatic ring having from 6 to 20 carbon atoms, or hetero aromatic ring. Substituent groups may be alkyl groups, and aryl groups, and in addition they may also be alkyl amino, dialkyl amino, aryl amino, diaryl amino, alkylthio, aryloxy, alkoxy, hydroxy, acyloxy, carboxyl, carboalkoxy, carboaryloxy, acyl, sulfonyl and sulfonyl amide, which may optionally have one or more substituents.

G¹ and G² can be the same or different and can each represent a hydrogen atom, a cyano group, an alkoxycarbonyl group, a substituted alkoxy carbonyl group, an aryloxy carbonyl group, a substituted aryloxy carbonyl group, an acyl group, a substituted acyl group, an aryl carbonyl group, a substituted aryl carbonyl group, an alkyl thio group, an aryl thio group, an alkyl sulfonyl group, an aryl sulfonyl group, or a fluoro alkyl sulfonyl group. However, G¹ and G² can not both be simultaneously hydrogen. G¹ and G² may combine with the carbon atom to which they are bonded to form a ring of non-metallic atoms.

When G¹ and G² form a ring of non-metallic atoms togehter with the carbon atom to which they are bonded, the ring may be one of the merocyanine dyes conventionally used as acidic nuclei, examples of which are barbituric acid nuclei like 1,3-diethyl-2-thiobarbituric acid, and rhodanine nuclei such as 3-ethyl rhodanine.

The variable n is 0 or 1.

In order for the dye residue having an absorption coefficient of greater than 1000 on the long wavelength side of 360 nm to be used as the light absorbing portion of the novel napthaquinone diazide of the present invention, it is necessary for there to be at least one functional group to form a bond to connect the light absorbing portion to the diazide group, for example, a carboxyl group, a hydroxyl group, an amino group, a sulfonyl group, an isocyanate group, a thioisocyanate group, or a thiol group.

The quinone diazide residue represented by Q can be the compounds of Kosar, *Light Sensitive Systems*, Volume 7 (John Wiley & Sons Inc. 1965), and those of v. Ershov, G. Nikitorov, *Quinone Diazides* (Elsevier Scientific Publishing Co. 1981). Specific examples of such quinone diazide compounds are p-quinone diazide compounds such as p-quinone-(1,4)-diazide, p-iminoquinone diazide, and napthaquinone-(1,4)-diazide, and ortho quinone diazide compounds such as napthaquinone-(1,2)-diazide, benzoquinone-(1,2)-diazide, etc. However, in order to be used in the present invention, it is necessary that these quinone diazide groups have at least one functional group to form a bond and connect to the light absorbing portion, such as a carboxyl group, a hydroxy group, an amino group, a sulfonyl group, an isocyanate group, a thioisocyanate group, or a thiol group.

$L^1$, $L^2$ and $L^3$ are connecting groups which connect S and Q with a covalent bond. However they do not directly conjugate S and Q. The following can be named as bond components included in the from among the bond component connecting groups represented by $L^1$, $L^2$ and $L^3$: ester bonds (—$CO_2$—), amide bonds (—CONH—), urea bonds (—NHCONH—), thiourea bonds (—NHCSNH—), sulfonyl ester bonds (—SO'—), sulfonamide bonds (—$SO_2$NH—), ureido bonds (—NH-$CO_2$—), thioureido bonds (—NHCSO—), carbonate bonds (—$OC_2$—), ether bonds (—O—), thioether bonds (—S—), and amino bonds (—NH—).

In order to make the energy transmission efficient between the excited dye portion and the quinone diazide portion, $L^1$ includes 2-20 atoms when going in the direction from S to Q, and preferably includes 2-10 atoms. $L^2$ and $L^3$, when added together, include 4-30 atoms when going in the direction from S to Q, and preferably include from 6-20 atoms.

The novel quinone diazide used in the present invention may be any of the examples recorded below. However, the present invention is of course not limited to the below examples.

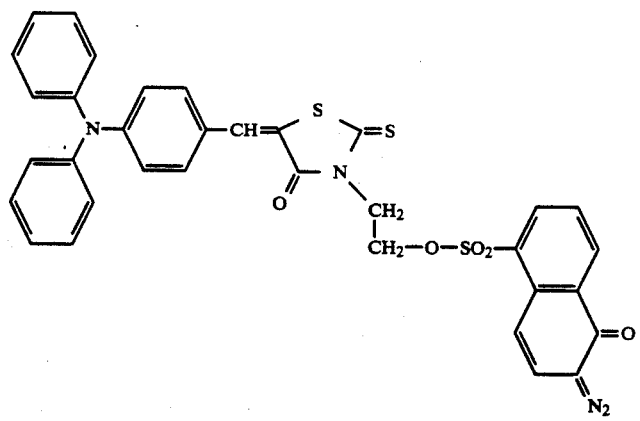

(1)

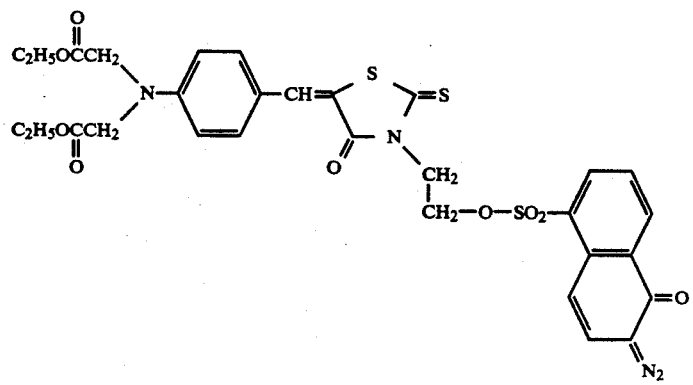

(2)

-continued
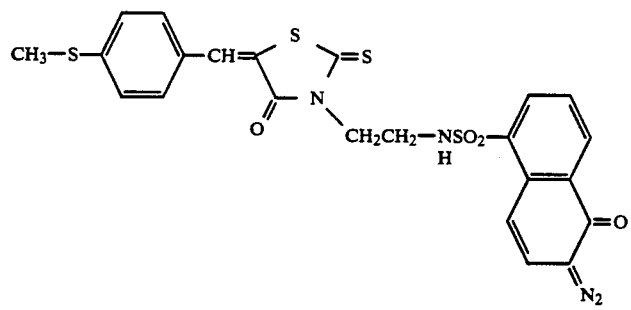
(3)
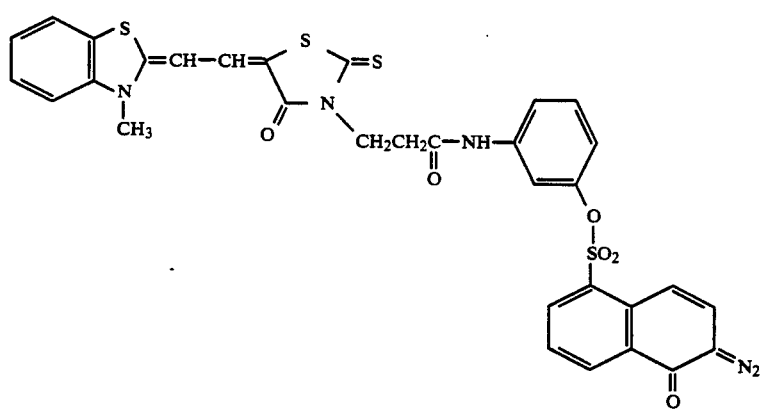
(4)
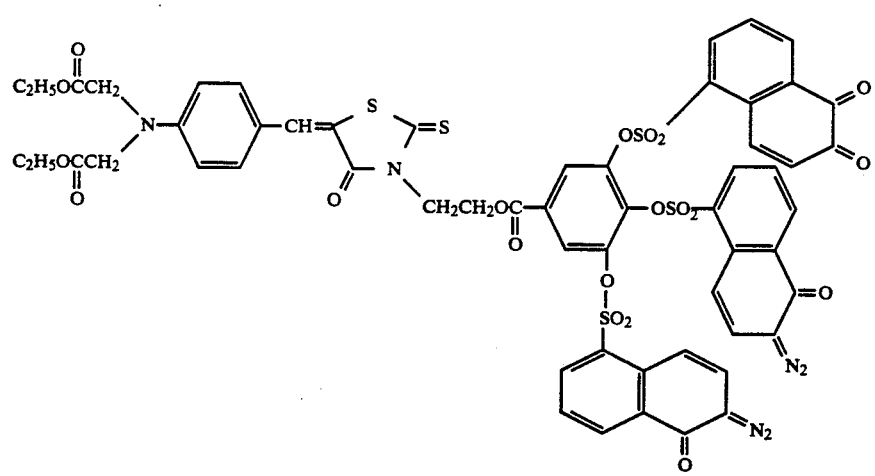
(5)
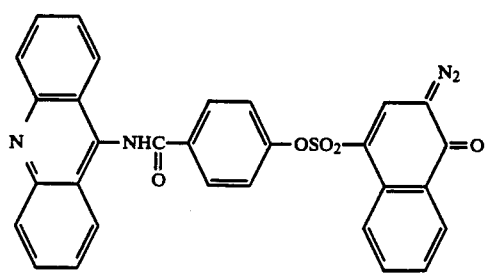
(6)

-continued
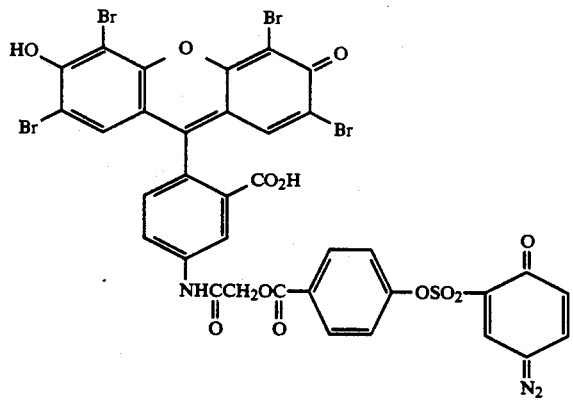 (7)
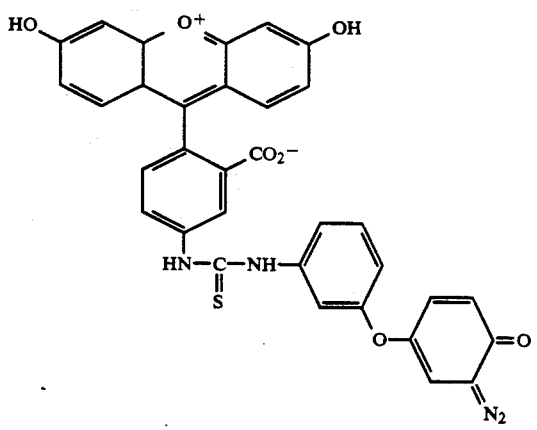 (8)
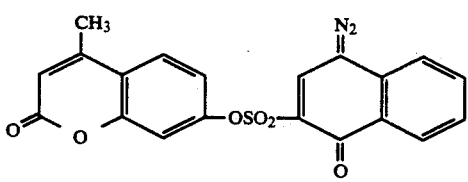 (9)
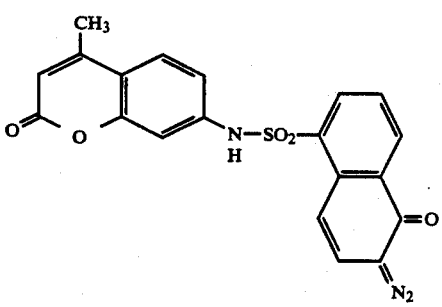 (10)
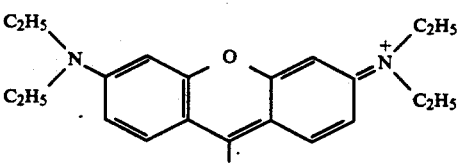 (11)

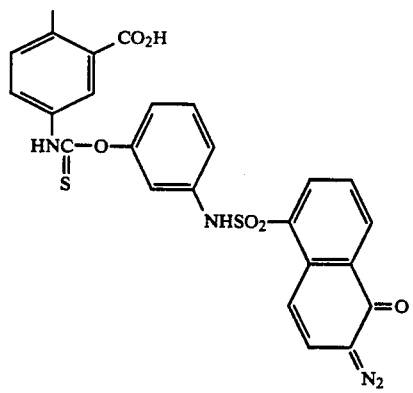
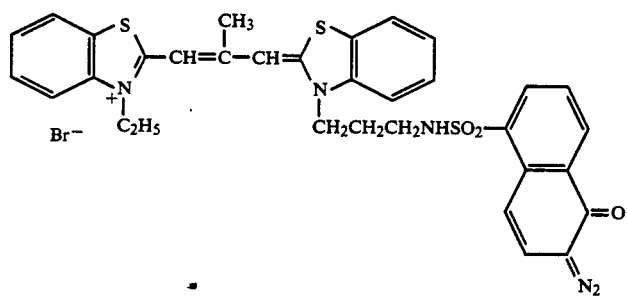
(12)
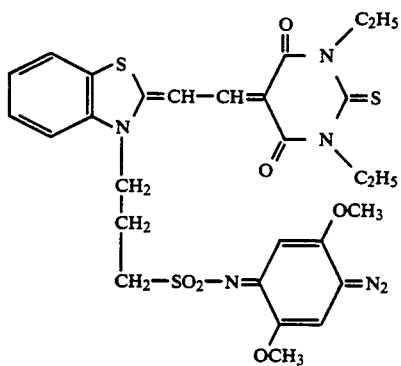
(13)
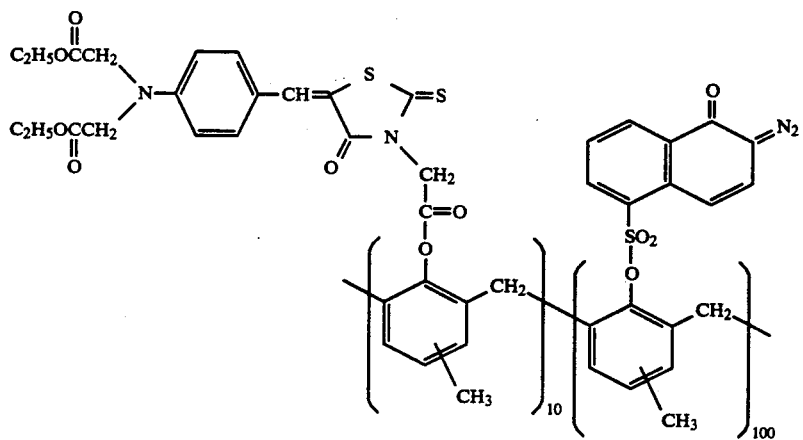
(14)

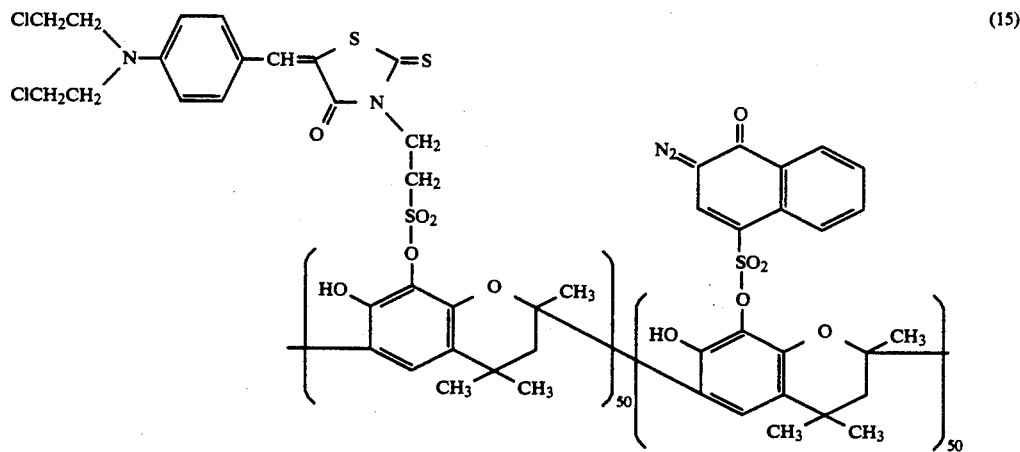
(15)
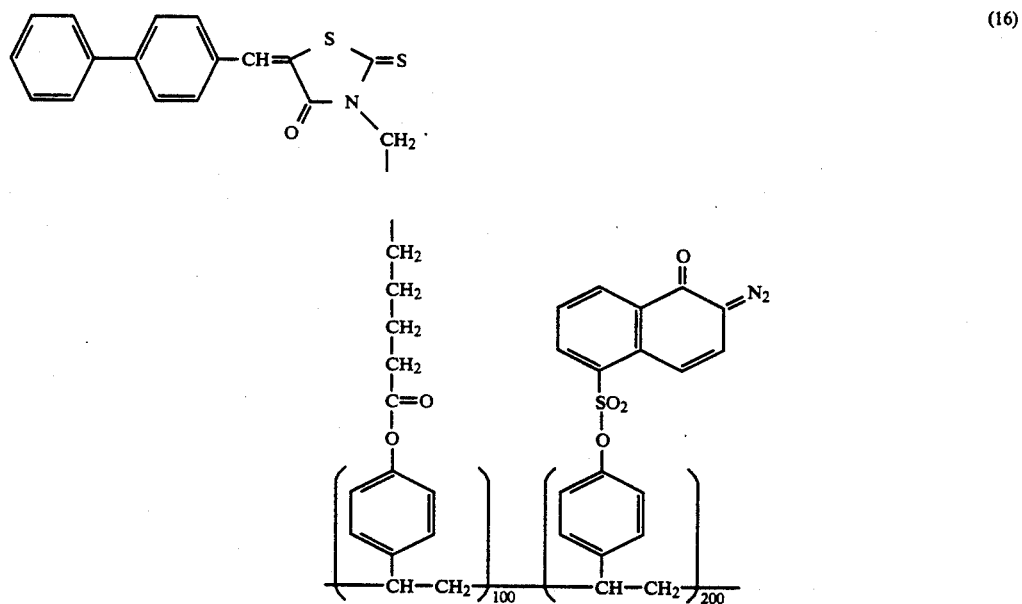
(16)
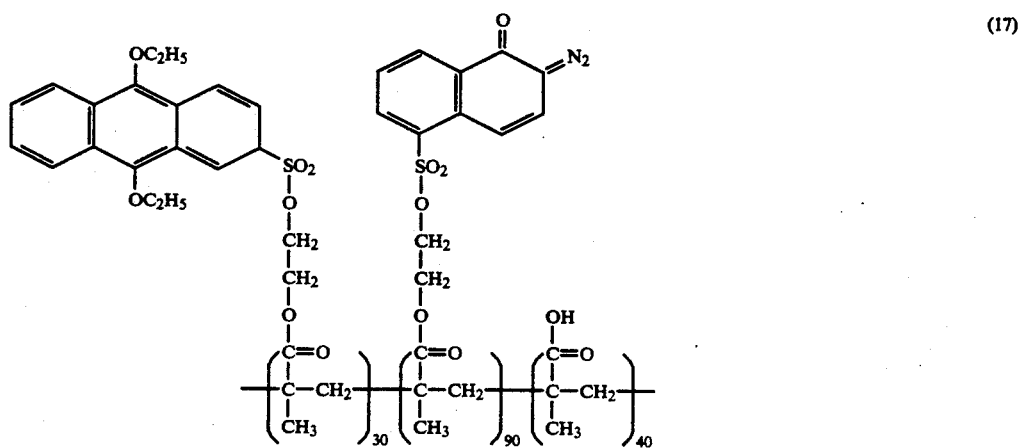
(17)

-continued

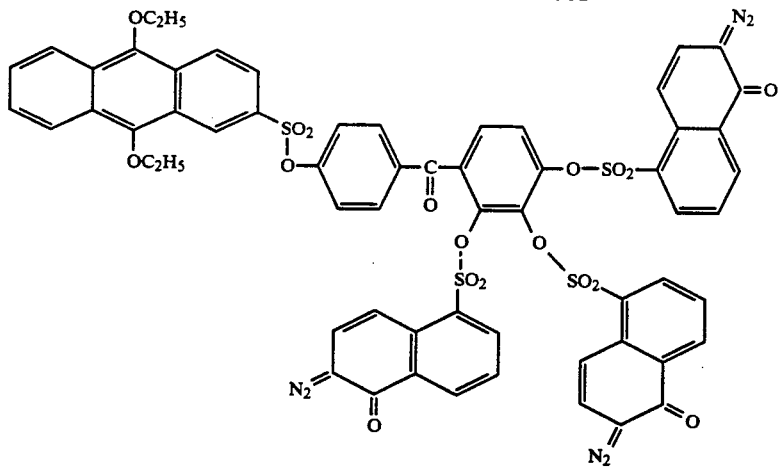

(18)

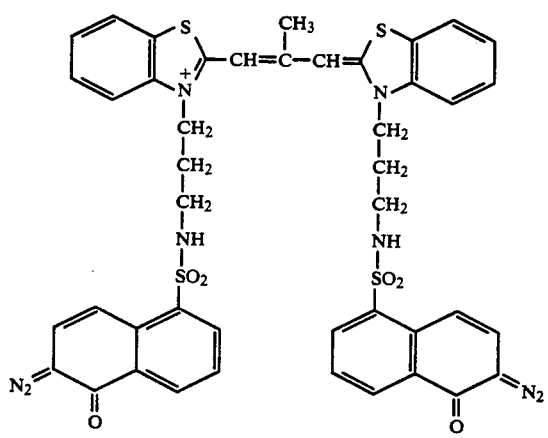

(19)

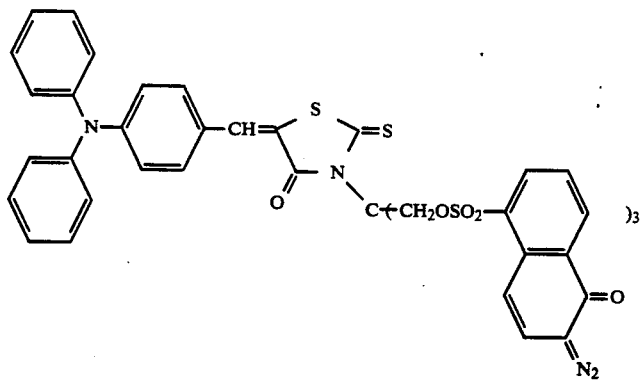

(20)

The novel quinone diazide compounds of the present invention can be prepared by condensing a light-absorbing compound having hydroxyl or amino group with an o-naphthoquinone diazide compound having sulfonyl chloride group. More specifically, one can use a conventional condensation reaction between an alcohol or an amine and a sulfonyl chloride as disclosed in S. R. Sandler, "Organic Functional Group Preparations", Second Ed., Academic Press, (1983), Vol. 1, page 630.

In addition, in order to connect a quinonediazide and a dye, one can use a reaction between an amine and an isocyanate to prepare an urea bond as disclosed in S. R. Sandler, "Organic Functional Group Preparations", First Ed., Academic Press, (1971), Vol. 2, page 139.

The light-sensitive compositions including the novel quinone diazide compounds of the present invention are particularly used, when mixed with alkali-soluble resins, in the photosensitive layers of presensitized plates for use in making lithographic printing plates (PS plates) and in photo-resists. When mixed with alkali soluble resins, the amount of the novel quinone diazide compound of the present invention is, based on the total weight of the light-sensitive composition, appropriately 5-80% by weight, preferably 10-40% by weight.

With respect to resins which are soluble in alkali, resins which have this property are novolac resins, for example, phenol/formaldehyde resins; cresolformaldehyde resins such as m-cresol/formaldehyde resin, p-cresol/formaldehyde resin, p- and m- mixture cresol/formaldehyde resin, phenol/cresol (p-, m- or mixtures of p- and m-)/formaldehyde resins; phenol/denatured xylene resins; polyhydroxy styrene; polyhalogenated hydroxy styrene; phenolic hydroxy group-containing acrylic resins like those described in Japanese Kokai No. Sho 51-34711; the sulfonamido group-containing acrylic or urethane resins described in Japanese Kokai No. Hei 2-866; and various other high molecular alkali-soluble compounds.

Other acrylic resins may be addition polymers having carboxylic acid groups on the side chains, such as, for example methacrylic acid copolymers, acrylic acid copolymers, itaconic acid copolymers, crotonic acid copolymers, and partially esterified maleic acid copolymers, etc., as disclosed in Japanese Kokai Nos. Sho 59-44615, Sho 54-34327, Sho 58-12577, Sho 54-25957, Sho 54-92723, Sho 54-53836, and Sho 59-71048. Also used are acidic cellulose derivatives having carboxylic acid groups on the side chains. In addition, one can use addition polymers having hydroxyl groups to which a cyclic acidic anhydride is added. Particularly preferred are copolymers of benzoyl (meth)acrylate, (meth)acrylic acid and optional addition polymerizable vinyl monomers; or copolymers of allyl (meth)acrylate, (meth)acrylic acid and optional addition polymerizable vinyl monomers.

These alkali-soluble high molecular compounds preferably have a weight average molecular weight of 500 to 200,000.

Such alkali-soluble high molecular compounds are used in an amount of 80% by weight or less of the total weight of the composition.

In order to improve the ink receptivity of image areas, it is also preferable to use a condensate of formaldehyde and a phenol substituted by an alkyl group having 3 to 8 carbon atoms such as t-butylphenol/formaldehyde resin and octyl phenol/formaldehyde resin as disclosed in U.S. Pat. No. 4,123,729.

The composition of the present invention may contain a cyclic acid anhydride for improving the sensitivity, an agent for obtaining a visible image immediately after exposure, a dye for coloring the image and a filler. The cyclic acid anhydrides include phthalic anhydride, tetrahydrophthalic anhydride, hexahydrophthalic anhydride, 3,6-endoxy-$\Delta^4$-tetrahydrophthalic anhydride, tetrachlorophthalic anhydride, maleic anhydride, chloromaleic anhydride, α-phenylmaleic anhydride, succinic anhydride and pyromellitic anhydride as described in U.S. Pat. No. 4,115,128. When 1 to 15% by weight, based on the whole composition, of the cyclic acid anhydride is incorporated thereinto, the sensitivity of the composition can be increased to at most three times higher. A typical example of the agents for obtaining a visible image immediately after exposure is an organic dye capable of forming a salt with a photosensitive composition capable of releasing an acid upon exposure. In particular, they include a combination of a salt-forming organic dye with an o-naphthoquinone diazide-4-sulfonic acid halide as described in U.S Pat. No. 3,969,118 and Japanese Kokai No. 53-8128 and a combination of a trihalomethyl compound with a salt-forming organic dye as described in U.S. Pat. Nos. 4,160,671 and 4,232,106. The colorants for the image include also dyes other than the above-described salt-forming organic dyes. Examples of the preferred dyes including also the salt-forming organic dyes are oil-soluble dyes and basic dyes such as Oil Yellow #101, Oil Yellow #130, Oil Pink #312, Oil Green BG, Oil Blue BOS, Oil Blue #603, Oil Black BY, Oil Black BS and Oil Black T-505 (which are products of Orient Kagaku Kogyo Co., Ltd.), victoria Pure Blue, Crystal Violet (CI 42555), Methyl Violet (CI 42535), Rhodamine B (CI 145170B), Malachite Green (CI 42000) and Methylene Blue (CI 52015) and more preferably those dyes described in Great Britain Patent No. 2192729. A total amount of the acid generating agents and the dyes ranges from about 0.3% to about 5% by weight based on the total weight of the composition.

The composition of the present invention is dissolved in a solvent in which the above ingredients are soluble, and the solution is applied to a support. The solvents usable herein include, for example, ethylene dichloride, cyclohexanone, methyl ethyl ketone, ethylene glycol, ethylene glycol monomethyl ether, ethylene glycol monoethyl ether, 2-methoxyethyl acetate, 1-methoxy-2-propanol, 1-methoxy-2-propyl acetate, toluene, ethyl acetate, methyl lactate, ethyl lactate, dimethylsulfoxide, N,N-dimethylformamide, N,N-dimethylacetamide, water, N-methylpyrrolidone, tetrahydrofurfuryl alcohol, acetone, diacetone alcohol, methanol, ethanol, isopropanol and diethylene glycol dimethyl ether.

These solvents are used either singly or in the form of a mixture of them. The concentration (solid content) of the solution is 2 to 50% by weight. The amount of the solution to be applied to the support varies depending on the use. For example, in the production of a PS plate, the amount of the coating is usually and preferably 0.5 to 3.0 g/m$^2$ (in terms of the solid). As the amount of the coating is reduced, the photosensitivity is increased, but the properties of the photosensitive film are impaired.

In order to improve coatability and uniformity of the photosensitive layer, a surfactant such as a fluorine-containing surfactant disclosed in U.S. Pat. Nos. 3,787,351, 4,487,823, 4,504,567 and 4,822,713 may be added to the composition of the invention.

The amount of the surfactant to be added is preferably from 0.01 to 1 % by weight, more preferably from 0.05 to 0.5 % by weight based on the total weight of the photosensitive composition.

The support includes, for example, papers; papers laminated with a plastic (such as polyethylene, polypropylene or polystyrene); metal sheets such as aluminum (including also aluminum alloys), zinc and copper sheets; plastic films such as cellulose diacetate, cellulose triacetate, cellulose propionate, cellulose butyrate, celulose acetate butyrate, cellulose nitrate, polyethylene terephthalate, polyethylene, polystyrene, polypropylene, polycarbonate and polyvinyl acetal; and papers and plastaic films having a coating film of the above-described metal formed by lamination or vacuum deposition. Among these supports, an aluminum sheet is particularly preferred, because it has a quite high dimensional stability and is inexpensive. Further, a composite film comprising a polyethylene terephthalate film having an aluminum sheet bonded therewith as described in British Pat. No. 1,329,714 is also preferred.

When the support has a metallic surface, particularly a aluminum surface, it is preferably surface-treated by graining, by immersion in an aqueous solution of sodium silicate, potassium fluorozirconate or a phosphoric acid or by anodic oxidation.

Suitable developers for the photosensitive composition of the present invention are aqueous solutions of an alkali such as sodium silicate, potassium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium bicarbonate, aqueous ammonia or tetramethyl ammonium hydroxide. It is used in such an amount that the concentration thereof would be 0.1 to 10% by weight, preferably 0.5 to 5% by weight.

The light sources usable for the exposure include, for example, a carbon arc lamp, mercury lamp, xenone lamp, tungsten lamp, metal halide lamp, various lasers such as visible and near infrared ones, luminescent light and sun light.

The following synthetic examples and examples will further illustrate the present invention, which by no means limit the scope of the present invention.

SYNTHETIC EXAMPLE 1

Synthesis of Compound (1)

Compound (1) is synthesized from compound (A) having the light absorbing portion shown in the following formula, and 1,2-naphthoquinone diazide-5-sulfonyl chloride.

The synthetic method is recorded below.

Compound (A) (2.3 g) and 1,2-napthoquinone diazide-5-sulfonyl chloride (5.4 g) were dissolved in 100 ml of methylene chloride under stirring.

The reaction was maintained at a temperature of 4°-5° C. under cooling with ice-water, and a solution of 2.6 g 4(N,N-dimethylamino) pyridine in 100 ml methylene chloride was added dropwise. After the dropwise addition was completed, stirring was continued for 2 hours.

To the reaction liquid was added 0.5 ml acetic acid, and the reaction liquid was extracted with 200 ml water. The methyl chloride layer was dried with $Na_2SO_4$ and filtered. The solvent was removed from the filtrate with an evaporator, the material is purified by column chromatography (silica gel: methylene chloride), and 2.2 g of Compound (1) was obtained.

Melting point (decomposition) 120°-130 C.
Mass Spectrum (SIMS method) m/e: 664.
IR Spectrum (KBr) $\nu cm^{-1}$ 2125, 1705, 1625.
UV Spectrum (in THF). $\lambda^{TH F}_{MA \, x} = 470$ nm ($\epsilon$: 3.70×10$^4$); $\lambda^{TH F}_{Ma \, x} = 335$ nm ($\epsilon$: 1.86×10$^4$).

| | Elemental Analysis | |
|---|---|---|
| | Calcd (%) | Found (%) |
| C | 61.43 | 61.39 |
| H | 3.64 | 3.62 |
| N | 8.43 | 8.41 |

HPLC (High Performance Liquid Chromatography)
Column: STR ODS-H
Flow Speed: 1 ml/min.
Solvent: $CH_3CN$:buffer = 85:15
(Buffer is phosphoric acid and $Et_3N$, each 1% in water)

| Compound | Retention time (min.) |
|---|---|
| (1) | 5.02 |
| (A) | 4.59 |
| 1,2-naphthoquinone-5-sulfonyl chloride | 2.05 |

SYNTHETIC EXAMPLE NO. 2

Synthesis of Compound (2).

Compound (2) is synthesized from the light-absorbingportion-containing compound (B) shown in the below formula and 1,2-naphthaquinone diazide-5-sulfonyl chloride.

The synthetic method is recorded below.

Using Compound (B) (1.0 g), 1,2-naphthoquinone diazide-5-sulfonyl chloride (2.38 g), and 4-(N,N-dimethylamino) pyridine (1.13 g), 1.16 g of Compound (2) was obtained by measn of the same operations as Synthetic Example No. 1.

Melting Point (Decomposition) 110°-115° C.
Mass Spectrum (SIMS method) m/e : 685
IR Spectrum (KBr) $\nu cm^{-1}$ 2010, 1715, 1710, 1700, 1620.
UV Spectrum (in THF): $\lambda^{TH F}_{Ma \, x} = 450$ nm ($\epsilon$: 3.43×10$^4$); $\lambda^{TH F}_{Ma \, x} 323$ nm ($\epsilon$: 1.72 ×10$^4$).

| | Elemental Analysis | |
|---|---|---|
| | Calcd (%) | Found (%) |
| C | 52.63 | 52.57 |
| H | 4.12 | 4.09 |
| N | 8.18 | 8.15 |

HPLC (High Performance Liquid Chromatography)
Column: STR ODS-H
Flow Speed: 1 ml/min.
Solvent: $CH_3CN$:buffer = 85:15
(Buffer is phosphoric acid and $Et_3N$, each 1% in water)

| Compound | Retention time (min.) |
|---|---|
| (2) | 2.26 |
| (B) | 2.03 |
| 1,2-naphthoquinone-diazide 5-sulfonyl chloride | 2.05 |

FLUORESCENCE MEASUREMENT EXAMPLE NO. 1

The below-described tetrahydrofuran solvent samples (i), (ii) and (iii) were prepared, and fluorescence measurements were conducted under the below conditions with a Hitachi model 850 fluorescence spectrometer.

Measurement conditions:
Excitation wavelength: 470 nm
Measurement temperature: Room temperature
Band pass:
  Excitation side 5 nm
  Receiving side 5 nm
(i) Light absorbing material (A) (2.2×10$^{-6}$ mole/l)
(ii) Present invention compound (1) (2.2×10$^{-6}$ mole/l)

(iii) Ligh absorbing material (A) and the naphthoquinone diazide shown below as (B) (each at $2.2 \times 10^{-6}$ mole/1).

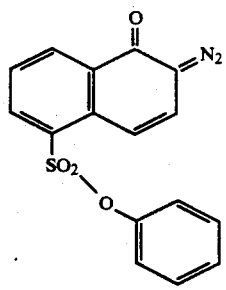
(B)

The same shaped broad-width emission was observed for samples (i), (ii) and (iii), but the emission intensity of (ii) was smaller than (i), and compared to the intensity of (i), (ii) had an intensity about half as large. On the other hand, the intensity of (ii) and (iii) was the same.

On a grained and anodized aluminum plate, a light-sensitive layer was set up so that the coated weight after drying of the below light-sensitive liquid was 2.0 g/m², and a PS plate was made.

| | |
|---|---|
| Phenol resin PR-50716 (Sumitomo Durez K.K.) | 0.25 g |
| Phenol resin 51600 B (Sumitomo Durez K.K.) | 0.35 g |
| Present invention quinone diazide Compound (1) | 0.21 g |
| N-methyl pyrrolidone | 6 g |
| Ethyl CELLOSOLVE acetate | 4 g |

A PS plate made in this manner was illuminated with an Oak K.K. Jetlight 2000 using an SC-46 filter which cut out light below 460 nm. Sensitivity measurements were made with a Fuji PS Step Guide (Fuji Film K.K., a step tablet in which the transmission density increases sequentially by 0.15 from a first step transmission density of 0.05 until a step of 15). After 100 seconds of exposure, the plate was developed with an aqueous sodium silicate solution with a SiO/NaO molar ratio of 1.74. The light-sensitive layer was completely removed until step 10, and from step 11, the light sensitive layer remained and a positive image was obtained.

After developing in this manner, sufficient rinsing with water and gumming-up in the usual manner, when printing, 50,000 printed sheets could be made.

COMPARATIVE EXAMPLES 1 AND 2

Replacing the following light sensitive substances for quinone diazide Compound (1), a PS plate was made according to completely the same method as Working Example 1.

| Comparative Example | Light-sensitive substances |
|---|---|
| 1 | (A) 0.13 g and (B) 0.10 g |
| 2 | (B) 0.10 g |

According to the same method by which Working Example (1) was exposed and developed, in both of the above Comparative Examples, the light-sensitive layer remained to the degree that no positive image could be obtained.

WORKING EXAMPLES 2-5

Quinone diazide Compound (1) was substituted with the following light-sensitive substances and PS plates were made according to completely the same method as Working Example 1.

| Working Example | Light-sensitive substance |
|---|---|
| 2 | (2) |
| 3 | (4) |
| 4 | (5) |
| 5 | (14) |

When exposed and developed in the same way as Working Example 1, a good positive image was obtained by each of the above.

The novel quinone diazide compound of the present invention have spectral sensitization with respect to visible light and are useful in visible light projection plates and as visible laser sensing materials.

While the present invention has been illustrated with several preferred embodiments and Working Examples, one of ordinary skill in the art will recognize that substitutions and improvements can be made while remaining within the scope and spirit of the present invention. The scope of the present invention is determined solely by the appended claims.

What is claimed is:

1. A quinone diazide compound of formula (I) or formula (II):

$$(S)_l-(L^1)_m-(Q)_n \quad (I);$$

$$-L^2(S))_o-(L^3(Q))_p- \quad (II);$$

wherein Q is a quinone diazide group; S is selected from the group of merocyanine dyes, cyanine dyes, acridine dyes, coumarine dyes, and arylidene dyes; $L^1$, $L^2$ and $L^3$ are connecting groups connecting S and Q, provided, however, that $L^1$, $L^2$ and $L^3$ do not conjugate S and Q; l is an integer of 1 to 3, m is 1 or 2, n is an integer of 1 to 8, o is an integer of 5 to 50, and p is an integer of 10 to 200.

2. A quinone diazide compound according to claim 1, said quinone diazide compound represented by formula (I).

3. A quinone diazide compound according to claim 1, said quinone diazide compound represented by formula (II).

4. A quinone diazide compound according to claim 1, wherein Q is selected from p-quinone diazide compounds and ortho quinone diazide compounds.

5. A quinone diazide compound according to claim 4, wherein Q is selected from p-quinone-(1,4)-diazide, p-iminoquinone diazide, napthoquinone-(1,4)-diazide, napthoquinone-(1,2)-diazide, and benzoquinone-(1,2)-diazide.

6. A quinone diazide compound according to claim 1, wherein $L^1$, $L^2$ and $L^3$ are selected from ester bonds, amide bonds, urea bonds, thiourea bonds, sulfonyl ester bonds, sulfonamide bonds, ureido bonds, thioureido bonds, carbonate bonds, ether bonds, thioether bonds, and amino bonds.

7. A quinone diazide compound according to claim 1, wherein S is an arylidene dye represented by the following formula (III):

$$R-(CH=CH)_r-CH=C(G^1)(G^2) \quad (III):$$

wherein R is a substituted or unsubstituted aromatic ring having from 6 to 20 carbona toms, or a hetero aromatic ring; $G^1$ and $G^2$ are the same or different, and each represents a hydrogen atom, a cyano group, an unsubstituted alkoxycarbonyl group, a substituted alkoxycarbonyl group, an unsubstituted alkoxycarbonyl group, a substituted alkoxycarbonyl group, an unsubstituted acyl group, a substituted acyl group, an unsubstituted aryl carbonyl group, a substituted aryl carbonyl group, an aryl thio group, an alkyl sulfonyl group, an allyl, sulfonyl group, or a fluoroalkyl sulfonyl group, provided however, that $G^1$ and $G^2$ cannot both be simultaneously hydrogen and $G^1$ and $G^2$ may combine with the carbon atom to which they are bonded to form a ring of non-metallic atoms; and n is 0 or 1.

8. A quinone diazide compound according to claim 7, wherein R is substituted with one or more of the groups selected from alkyl groups, aryl groups, alkyl amino, dialkyl amino, aryl amino, diaryl amino, alkylthio, aryloxy, alkoxy, hydroxy, acyloxy, carboxyl, carboalkoxy, carboaryloxy, acyl, sulfonyl, and sulfonyl amide.

9. A quinone diazide compound according to claim 7, wherein $G^1$ and $G^2$ together form an acidic merocyanine nuclei or a rhodanine nuclei.

10. A quinone diazide compound according to claim 9, wherein $G^1$ and $G^2$ together form 1,3-diethyl-2-thiobarbituric acid or 3-ethyl rhodamine.

11. A quinone diazide compound according to claim 1 selected from the group consisting of the following formulas:

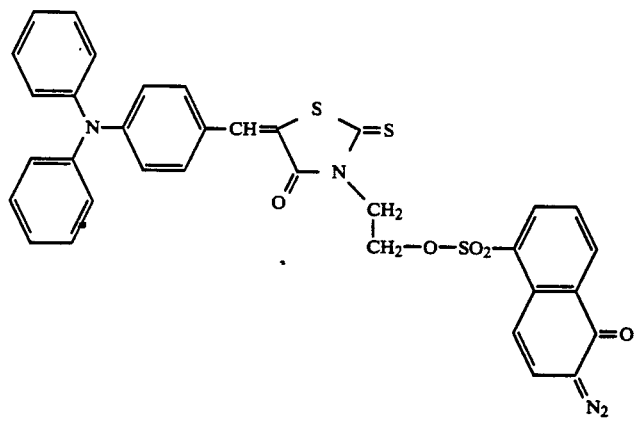

(1)

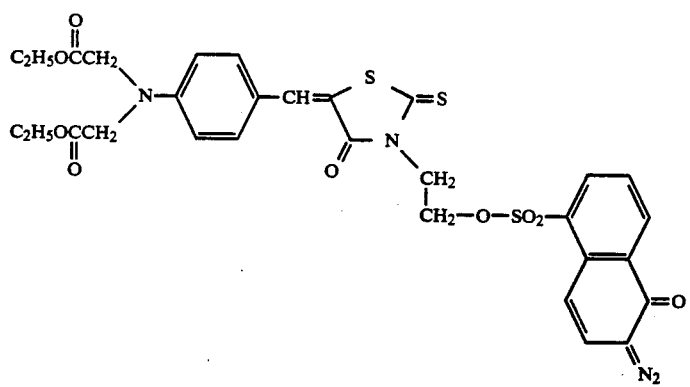

(2)

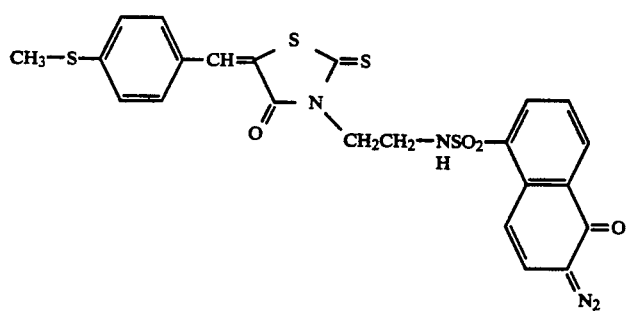

(3)

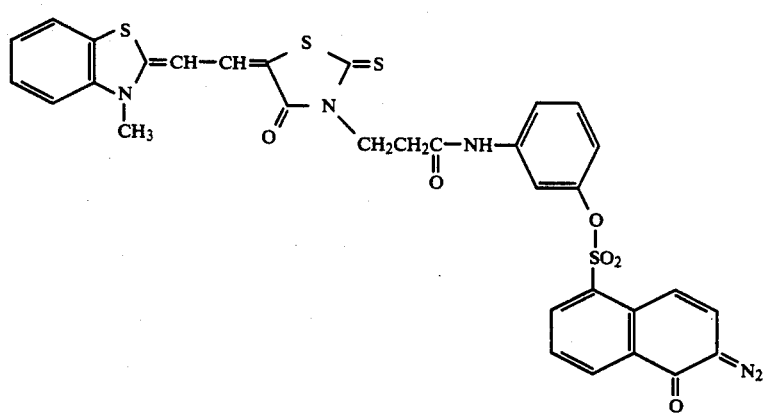
(4)
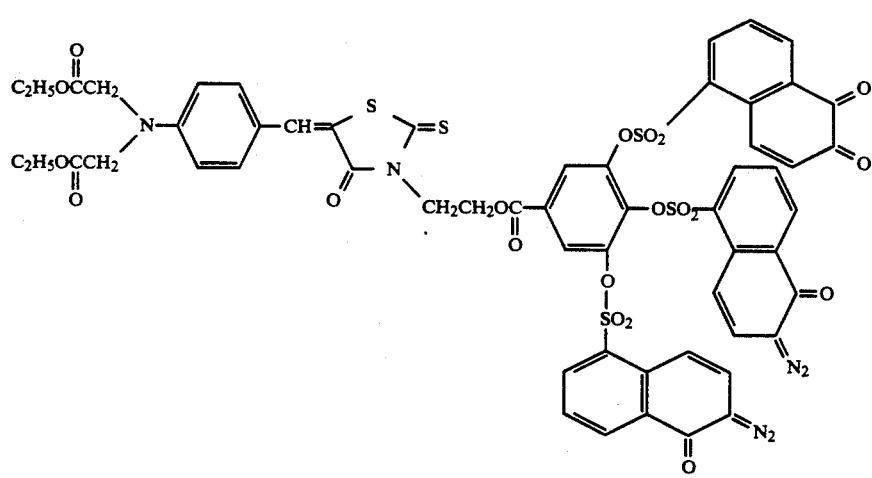
(5)
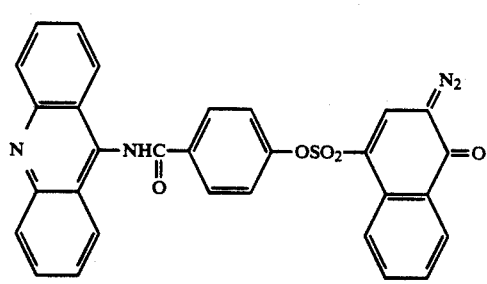
(6)
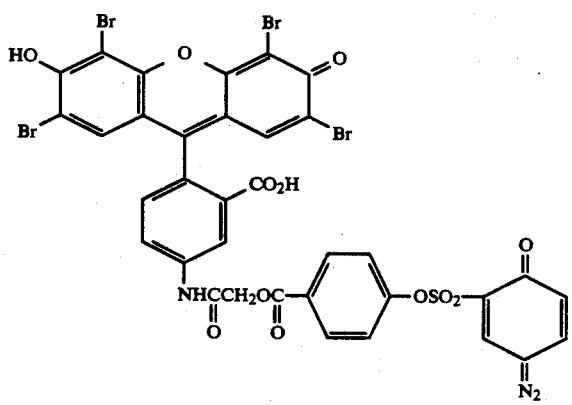
(7)

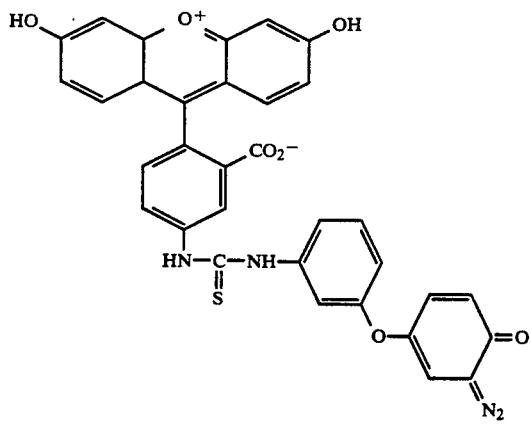
(8)
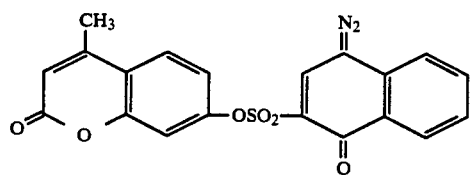
(9)
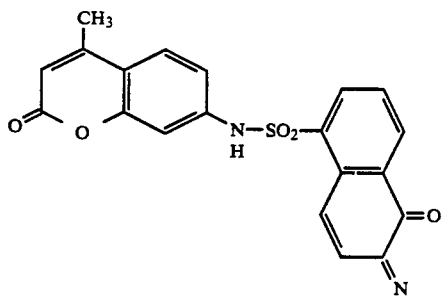
(10)
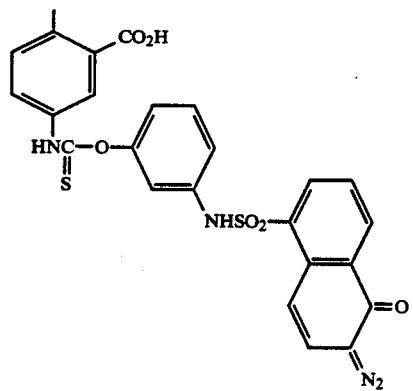
(11)

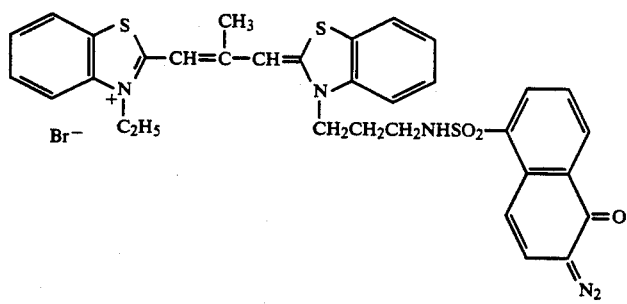
(12)
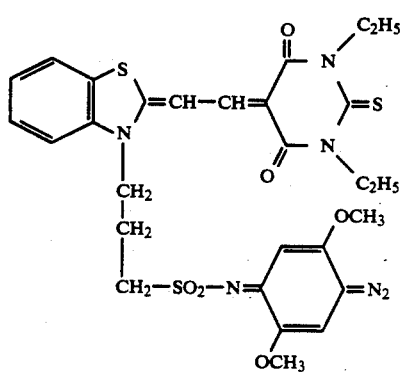
(13)
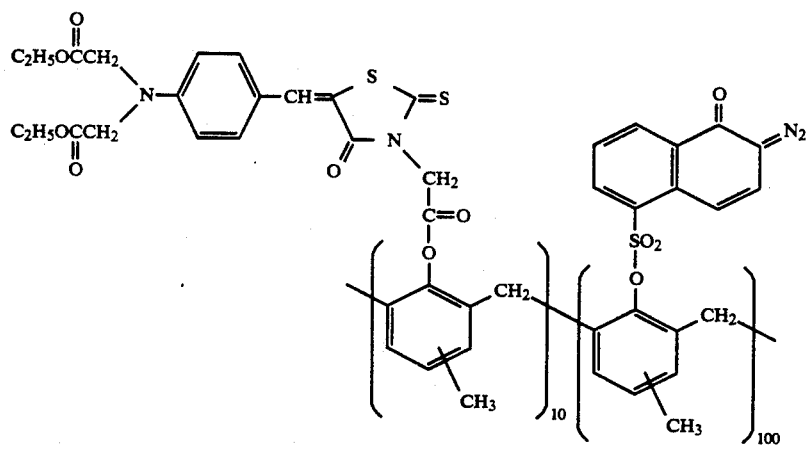
(14)
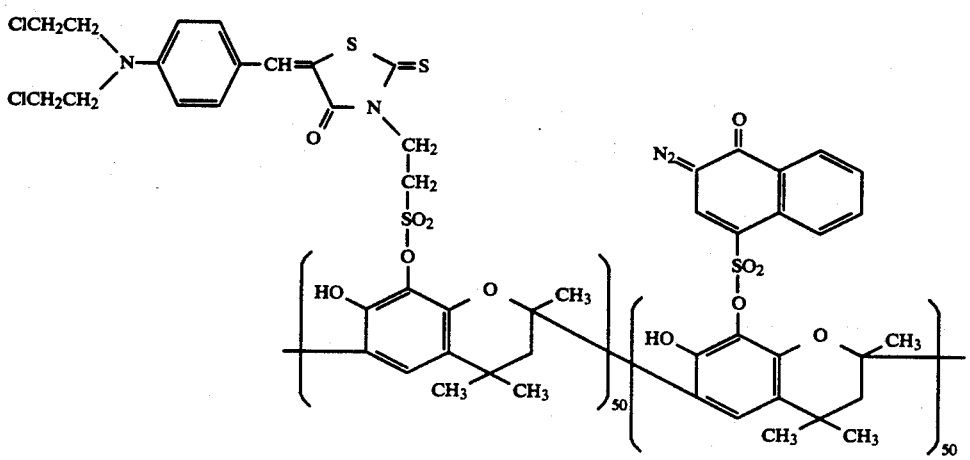
(15)

  (16)
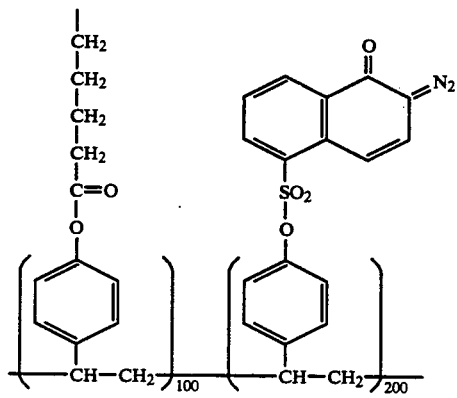  (17)
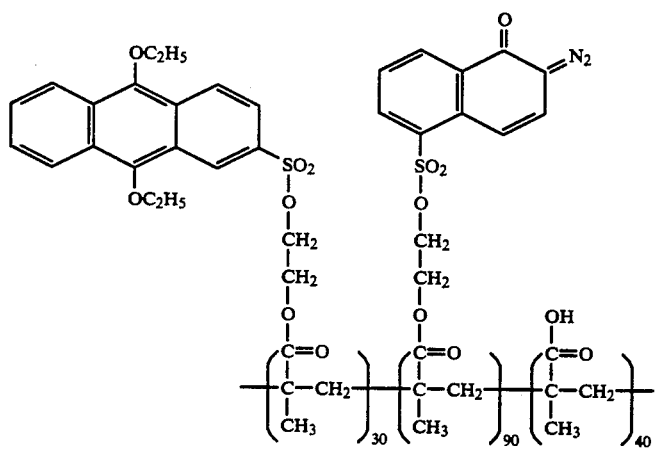
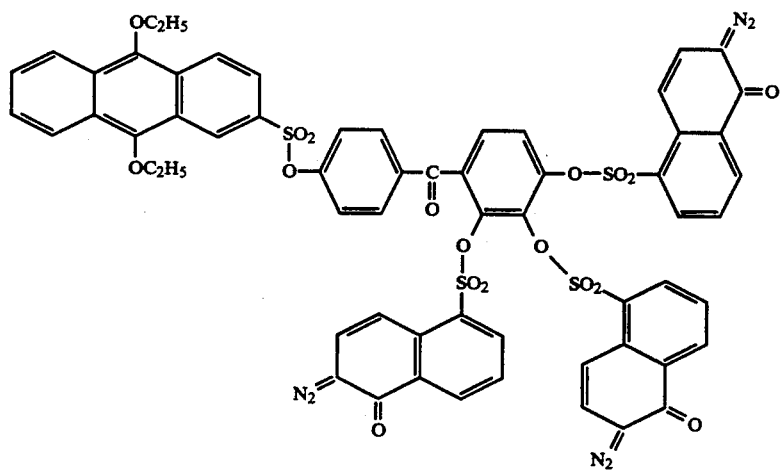  (18)

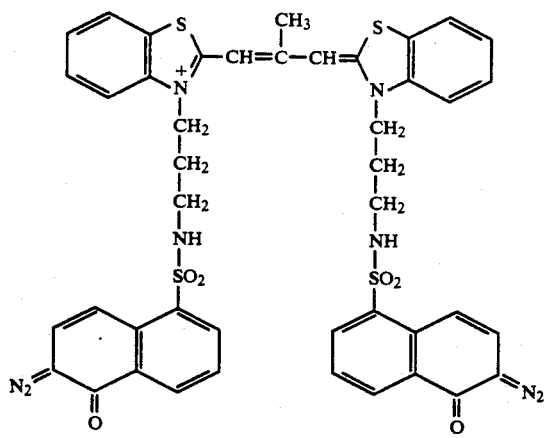
(19)
and
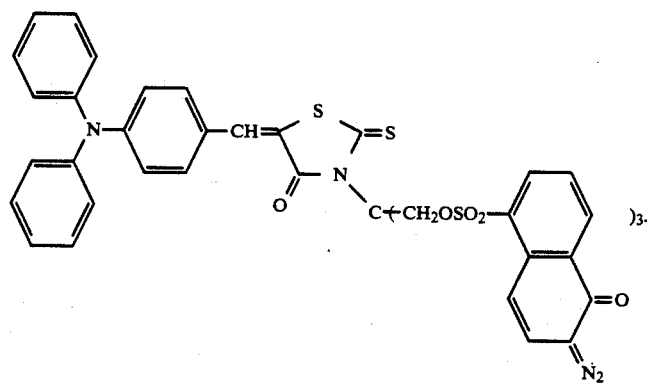
(20)